United States Patent [19]

Suzuki et al.

[11] Patent Number: 5,478,508
[45] Date of Patent: Dec. 26, 1995

[54] METHOD OF PRODUCING SEAMLESS CAPSULE

[75] Inventors: Toshiyuki Suzuki; Masayuki Ikeda; Takahiro Okuda, all of Tokyo, Japan

[73] Assignee: Freund Industrial Co., Ltd., Tokyo, Japan

[21] Appl. No.: 143,475

[22] Filed: Oct. 26, 1993

[30] Foreign Application Priority Data

Oct. 28, 1992 [JP] Japan .................................. 4-289205

[51] Int. Cl.$^6$ ...................... B29C 47/26; B01J 13/20; B65B 3/12
[52] U.S. Cl. ................ 264/4; 264/4.3; 264/4.4; 424/451; 426/96; 426/102; 426/592
[58] Field of Search ................... 264/4.3, 4.4, 4; 425/5; 424/451; 426/96, 102, 592

[56] References Cited

U.S. PATENT DOCUMENTS

| 3,361,632 | 1/1968 | Ross et al. ........................... 264/4 |
| 3,389,194 | 6/1968 | Somerville .......................... 264/4 |
| 3,423,489 | 1/1969 | Arens et al. ........................ 264/4 |
| 3,664,963 | 5/1972 | Pasin ................................. 264/4 X |
| 4,251,195 | 2/1981 | Suzuki et al. ..................... 425/5 X |
| 4,422,985 | 12/1983 | Morishita et al. ................. 264/4.4 |
| 4,481,157 | 11/1984 | Morishita et al. ................. 264/4.1 |
| 4,888,140 | 12/1989 | Schlameus et al. ............... 264/4.3 |
| 5,209,978 | 5/1993 | Kosaka et al. .................... 264/4.4 X |
| 5,330,835 | 7/1994 | Kikuchi et al. .................... 264/4.4 X |

FOREIGN PATENT DOCUMENTS

| 2336176 | 7/1977 | France . |
| 2746489 | 4/1979 | Germany . |
| 56-89833 | 7/1981 | Japan . |
| 3-52639 | 3/1991 | Japan . |
| 563807 | 7/1975 | Switzerland . |

*Primary Examiner*—Richard D. Lovering
*Attorney, Agent, or Firm*—Kane, Dalsimer, Sullivan, Kurucz, Levy, Eisele and Richard

[57] ABSTRACT

A process for producing a seamless capsule wherein a two-layer droplet is ejected from a double orifice type nozzle in an aqueous hardening liquid, and an outer layer of the droplet is hardened under cooling, the viscosity of the aqueous hardening liquid being made within the range of 20 to 100 mPa·s, and any difference in specific gravity between any two of the liquids of the layers ejected from the nozzle and the aqueous hardening liquid is made within 0.05.

7 Claims, 1 Drawing Sheet

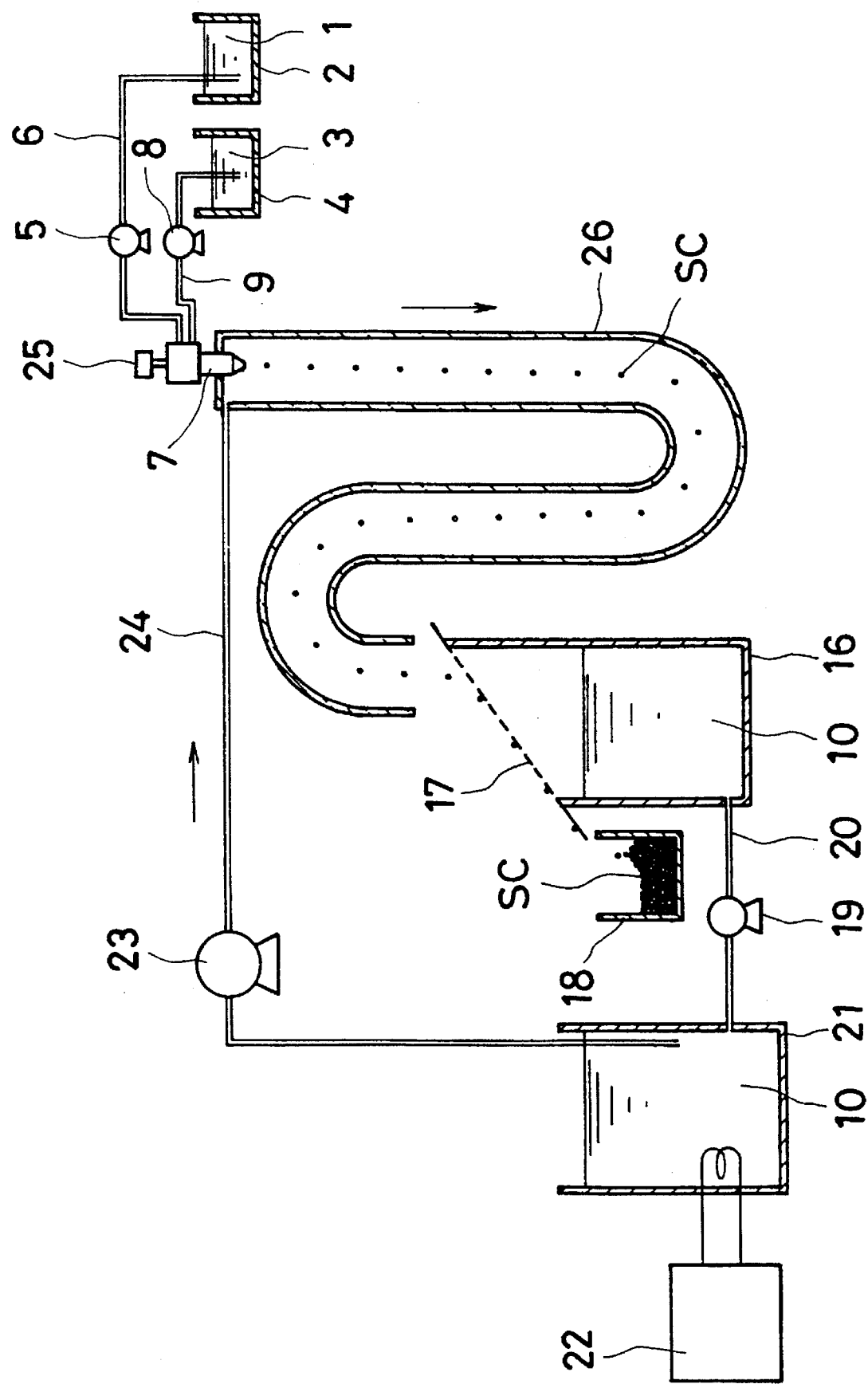

METHOD OF PRODUCING SEAMLESS CAPSULE

BACKGROUND OF THE INVENTION

1. Field of the Invention

This invention relates to a method of producing a seamless capsule, and more particularly to a method of producing a seamless capsule having a good shape and good preservability.

2. Related Art Statement

Conventionally, there has been widely known a method of producing a seamless capsule in which a concentric multilayer solution is ejected from a multiple nozzle of a multiple orifice type, such as a double orifice and a triple orifice, into a hardning liquid to form a multiple-layer droplet and at least an outermost layer of the droplet is solidified to produce a seamless capsule.

Among the seamless capsules, one which is of simplest structure and has been widely used is a two-layer capsule having single core as the inner layer, which is made with a double orifice. In producing the two-layer capsule, in many cases, an outer layer is hardened by cooling.

Constitution of the single core two-layer capsule can be generally classified into two types, i.e., one containing an aqueous liquid as a material encapsulated therein and the other containing an oily liquid. As the outer layer, a lipophilic material such as wax is used in the former type, and a hydrophilic material such as gelatin, alginate or agar in the latter type.

For producing such a single core two-layer capsule, cooling type solidification is employed except for the case of chemical reaction type solidification where, for example, sodium alginate in the outer layer is solidified in reaction with an aqueous solution of a calcium salt. As a hardening liquid in the cooling type solidification, water has been used for the capsule having the lipophilic outer layer whereas an oily hardening liquid such as vegetable oil or liquid paraffin has been used for the hydrophilic outer layer.

Among the single core two-layer capsules, with regard to the capsule containing an oily material as the core, there have been proposed a large number of production methods and constitutions of the capsule, mainly in the field of an oral refrigerant. However, with regard to the capsule containing an aqueous solution therein, sufficient investigation has not yet been carried out.

For example, in U.S. Pat. No. 3,389,194, there is disclosed an example where water is used both as the core solution and as the hardening liquid, and wax is used as the outer layer. However, it only discloses a principle and does not describe the conditions required for respective components.

Also, in Swiss Patent No. 563,807, there is disclosed a similar method as in the above U.S. Patent, using water as the core solution, a melted paraffin as the outer layer and water as the hardening liquid. However, there is no further detailed description with respect to each component.

In recent years, as to constitution of a seamless capsule containing an aqueous solution, there have been developments to another direction. For example, in Japanese Unexamined Patent Laid-Open No. 56-89833, in order to contain an aqueous solution in the gelatin capsule, there is disclosed a method of protecting the gelatin outer layer by adding tannin to the gelatin when the aqueous solution is not acidic or adding an enteric coating agent when the aqueous solution is acidic, and using an oily substance such as vegetable oil as the hardening liquid.

Also, in Japanese Unexamined Patent Laid-Open No. 3-52639, there is disclosed a method of interposing a fatty acid ester of sucrose (sucrose acetate isobutyrate) between the aqueous core solution and the gelatin outer layer, and similarly using an oily substance as the hardening liquid.

As described above, whereas the method of using water as the core solution, an oily substance such as paraffin as the outer layer and water as the hardening liquid has been proposed for a long time, it has not been used practically.

This is because the method involves serious defects that uneven thickness of layers, i.e., eccentricity of layers or pin hole is likely to occur in the course of producing a seamless capsule so that the encapsulated water is lost by evaporation and thus, the quality of the capsule product is not preserved. It is considered that unlike a material such as gelatin which has flexibility and solidifies gradually, the outer layer comprising paraffin, etc. tends to produce cracks easily and rapidly solidifies at a solidifying temperature, and therefore the above-described defects are caused.

Thus, there is difficulty in the process of forming an outer layer with wax so that the methods of using gelatin as the outer layer have been proposed as mentioned above.

However, in the method disclosed in Japanese Unexamined Patent Laid-Open No. 56-89833, water sealing property of the outer layer is insufficient and loss of the encapsulated water is unavoidable. Also, in the method disclosed in Japanese Unexamined Patent Laid-Open No. 3-52639, fatty acid ester of sucrose used as the intermediate layer has low melting point and the ester becomes liquid at the room temperature so that the loss of water in the core solution can not be prevented, making the method impractical.

Thus, these methods of improving the gelatin outer layer can not be applied to except for a core solution such as containing a large amount of glycerin or polyethylene glycol in addition to water. It is the present status that there has not yet been found a method of producing a seamless capsule encapsulating a solution which mainly comprises water and having preservability for a long period of time.

SUMMARY OF THE INVENTION

An object of the present invention is to provide a method of producing a seamless capsule which contains an aqueous solution therein and can be preserved for a long period of time.

Another object of the present invention is to provide a method of producing a seamless capsule having a good outer shape.

Still another object of the present invention is to provide a method of producing a seamless capsule having a uniform particle size and having an outer layer with a uniform thickness.

Among the inventions disclosed herein, representative ones will be briefly described as follows.

In principle, it is advantageous to constitute an outer layer by a lipophilic substance in order to produce a seamless capsule which seals water and can be preserved for a long time. Thus, the present inventors have intensively studied this type of constitution to find that for achieving above purposes, it is effective to satisfy either a condition that the viscosity of the hardening liquid is within 20 to 100 mPa·s or a condition that difference of the specific gravities between any two of three solutions, i.e., the core solution, the solution for an outer layer and the hardening liquid, is within 0.05, and when both the conditions are satisfied, more excellent results can be obtained, whereby accomplishing the present invention.

In one embodiment of the invention, the viscosity of the aqueous hardening liquid is set within 20 to 100 mPa·s.

Although the method of using water as the cooling and hardening liquid has been proposed for a long time as described above, the fact that the viscosity of the hardening liquid affects to the quality of the seamless capsule has never been known, and it has been found for the first time by the present inventors that the above range is suitable.

According to the investigation by the present inventors, if the viscosity of the aqueous hardening liquid is less than 20 mPa·s, a jet stream ejected from the orifice becomes unstable and oscillates irregularly, and thus, the size of the droplets varies in wide range or unevenness in wall thickness or eccentricity of the outer layer occurs. On the other hand, if it exceeds 100 mPa·s, it was found that resistance to the jet stream becomes large and its flow rate can not be set to a value suitable for practical production rate.

In order to set the viscosity of the aqueous hardening liquid within the above range, an aqueous solution containing a low molecular weight substance such as glycerol, polyglycerol, diethylene glycol, triethylene glycol, saccharides and sugar alcohols can be used. It, however, is preferred to use an aqueous solution of a water-soluble polymer.

This is because when a low molecular weight substance is used for getting an aqueous solution which has a viscosity belonging to the range defined in the present invention, It is necessary to make it a solution of considerable high concentration, causing undesirable problems such as increase of specific gravity of the solution and necessity of intensified washing of a formed capsule, while these disadvantages are not caused when a polymer substance is used.

As a water-soluble polymer, there may be mentioned (1) synthetic polymers such as polyvinyl alcohols, polyacrylic acids or salts thereof, polyacrylamides, carboxyvinyl polymers, polyvinyl pyrrolidones, polyvinyl methyl ethers, copolymers of vinyl acetate or vinyl ether with maleic anhydride, polyethylene glycols and polyoxyethylenes; and (2) modified products of cellulose or starch such as hydroxyethylcelluloses, hydroxypropylcelluloses, methylcelluloses, sodium carboxymethylcelluloses or mixed cellulose ethers of the above celluloses, starches, oxidized starches, dextrins, hydroxypropyl starches, carboxymethyl starches and starch phosphates.

A second embodiment of the invention is characterized by a combination of three solutions, the core solution, the outer layer solution and the hardening liquid, in which difference in specific gravities between any two of the three solutions is within 0.05.

As described above, although the method of using water as the cooling and hardening liquid has been proposed for long time, good seamless capsule can not be obtained when a substance such as paraffin is used as the outer layer. The present inventors have found that, relating to use of a substance having a small specific gravity such as paraffin as the outer layer, one of causes of the problem resides in difference in the specific gravities of the liquids, and the above characteristic feature of the invention was obtained.

If the difference of the specific gravities between any two solutions as mentioned above (i.e. the difference between the maximum specific gravity and the minimum specific gravity of the three solutions) exceeds 0.05, a thickness of the outer layer becomes nonuniform to cause uneven thickness or eccentricity, whereby strength of the capsule becomes weak and transudation of the water enclosed in the capsule becomes large.

The difference in the specific gravities between two solutions affects the shape of the droplet during the droplet contacts with the hardening liquid until the outer layer is hardened, and therefore, in the present invention, "specific gravities" means ones at those temperatures while the outer layer is being hardened, thus, the temperatures of respective solutions being, in principle, not equal.

The objects described above can be accomplished by either of the embodiments of the invention, though, when both embodiments of the invention are used in combination, more excellent result can be obtained.

In the present invention, a double orifice of a nozzle may be immersed in an aqueous hardening liquid, or the orifice may be positioned in the air so that droplets are jetted to fall dropwise into the hardening liquid. The former in-liquid type method is preferred since no impact is given to the ejected droplets.

In addition to the production of the seamless capsule containing an aqueous solution or a hydrophilic solvent therein, the method of the present invention can be used in encapsulating a solvent which does not dissolve an outer layer or a substance which solidifies by cooling.

As a material to be used for the outer layer, any material which does not dissolve in an aqueous hardening liquid but melts stably and solidifies by cooling can be adopted. Examples are waxes, oils, fats, paraffins, thermoplastic resins and the like.

The outer layer solution is lipophilic and, in most cases, different in characteristics from the other two solutions so that the specific gravity of the outer layer is also different from those of the other two solutions. In such a case, it is desirable to control the specific gravity of the outer layer solution within the range of the second embodiment of the invention by adding thereto a substance which is compatible with the outer layer solution and has a different specific gravity therefrom.

BRIEF DESCRIPTION OF THE DRAWING

The above and other objects and features of the present invention will become more apparent when referred to the following descriptions given in conjunction with the accompanying drawing, and:

FIG. 1 is a schematic view showing one example of an apparatus for producing a seamless capsule for practicing the process of the present invention.

DETAILED DESCRIPTION OF THE PREFERRED EMBODIMENTS

First, referring to FIG. 1, one example of an apparatus for producing a seamless capsule will be explained. This apparatus has a structure of the nozzle-in-liquid type, and a droplet ejecting portion of a double orifice of a nozzle is dipped in an aqueous hardening liquid.

That is, in the apparatus for producing a seamless capsule shown in FIG. 1, a solution to be encapsulated, i.e., a core solution 1 for forming a seamless capsule SC is stored in a tank 2 for the core solution, and an outer layer solution 3, i.e., a coating film solution for enveloping the core solution 1 is stored in a tank 4 for the outer layer solution.

The core solution 1 is transmitted by pressure by a pump 5 from the tank 2 to a nozzle 7 having a double orifice through a piping route 6. On the other hand, the outer layer solution 3 is transmitted by pressure by a pump 8 from the tank 4 to the nozzle 7 through a piping route 9.

Since the apparatus of the present example has the structure of the nozzle-in-liquid type, the nozzle 7 having the double orifice structure is inserted into an inlet portion of a main flow path pipe 26 forming a main flow path for supplying an aqueous hardening liquid 10. The double orifice structure is constructed so that, into the aqueous hardening liquid 10, the core solution 1 and the outer layer solution 3 are ejected from the double orifice, and the outer layer solution envelopes the whole surface of the core solution.

Further, in the present example, there is adopted a structure in which the nozzle 7 of the double orifice type is vibrated by a vibrator (vibrating means) 25.

Accordingly, in the present apparatus, owing to the vibration applied to the nozzle 7 by the vibrator 25, the core solution 1 and the outer layer solution 3 ejected from the nozzle 7 are formed as two-layer droplets in the aqueous hardening liquid 10 of the main flow path pipe 26, and as the droplets flow in the main flow path pipe 26, they are solidified by the effect of the aqueous hardening liquid 10 and formed as seamless capsules SC.

The seamless capsules SC thus formed flow down from an outlet end of the main flow path pipe 26 onto an inclined porous member 17 of a separation tank 16 together with the aqueous hardening liquid 10, are separated from the aqueous hardening liquid 10 by the porous member 17 and roll down on the inclined surface of the porous member 17 to be collected in a product recovering container 18.

In the present apparatus, the aqueous hardening liquid 10 in the separation tank 16 is transmitted by pressure by a pump 19 to a cooling tank 21 through a piping route 20. After the aqueous hardening liquid 10 in the cooling tank 21 is cooled to a predetermined temperature by a cooler 22, it is returned into the main flow path pipe 26 by a pump 23 through a piping route 24.

EMBODIMENTS 1 TO 3

Seamless capsules were produced by using the device shown in FIG. 1.

Embodiments 1, 2, and 3 of the invention were effected, embodiments 3 constituting the combination of embodiments 1 and 2.

In all of Embodiments 1 to 3 and Comparative example, production was performed so that the capsule was 3.0 mm in diameter, the outer layer thickness was 130 μm, the amount of the core solution was 14.5 mg and the capsule production rate was 15 capsules/sec.

Embodiments 1 to 3 and Comparative example are further described in Tables 1 to 4, respectively.

TABLE 1

| | Composition | | Flow rate or Flow speed | Viscosity | Specific gravity | Temperature |
|---|---|---|---|---|---|---|
| | | Embodiment 1 | | | | |
| Core liquid | Purified water: | 100 parts | 0.22 ml/sec | — | 1.000 | 22.6° C. |
| Outer layer solution | Fatty acid ester of glycerin (melting point 42° C.): | 70 parts | 0.10 ml/sec | — | 0.943 | 70.0° C. |
| | Fatty acid ester of sucrose (melting point 36° C.): | 30 parts | | | | |
| Hardening soution | Purified water: | 99 parts | 9 cm/sec | 60 mPa · s | 1.005 | 32.0° C. |
| | HPC-H:* | 1 parts | | | | |

*Nippon Soda Co. Ltd., see catalog for NISSO HYDROXY PROPYL CELLULOSE, also mentioned in the Pharmacopeia of Japan.

TABLE 2

| | Composition | | Flow rate or Flow speed | Viscosity | Specific gravity | Temperature |
|---|---|---|---|---|---|---|
| | | Embodiment 2 | | | | |
| Core liquid | Purified water: | 100 parts | 0.22 ml/sec | — | 1.000 | 22.6° C. |
| Outer layer solution | Fatty acid ester of glycerin (melting point 42° C.): | 50 parts | 0.10 ml/sec | — | 0.980 | 70.0° C. |
| | Fatty acid ester of sucrose (melting point 36° C.): | 50 parts | | | | |
| Hardening soution | Purified water: | 99.75 parts | 9 cm/sec | 6 mPa · s | 1.002 | 32.0° C. |
| | HPC-H:* | 0.25 parts | | | | |

*Nippon Soda Co. Ltd., see catalog for NISSO HYDROXY PROPYL CELLULOSE, also mentioned in the Pharmacopeia of Japan.

TABLE 3

Embodiment 3

| | Composition | | Flow rate or Flow speed | Viscosity | Specific gravity | Temperature |
|---|---|---|---|---|---|---|
| Core liquid | Purified water: | 100 parts | 0.22 ml/sec | — | 1.000 | 22.6° C. |
| Outer layer solution | Fatty acid ester of glycerin (melting point 42° C.): | 50 parts | 0.10 ml/sec | — | 0.980 | 70.0° C. |
| | Fatty acid ester of sucrose (melting point 36° C.): | 50 parts | | | | |
| Hardening soution | Purified water: HPC-H:* | 99 parts 1 parts | 9 cm/sec | 6 mPa · s | 1.005 | 32.0° C. |

*Nippon Soda Co. Ltd., see catalog for NISSO HYDROXY PROPYL CELLULOSE, also mentioned in the Pharmacopeia of Japan.

TABLE 4

Comparative example

| | Composition | | Flow rate or Flow speed | Viscosity | Specific gravity | Temperature |
|---|---|---|---|---|---|---|
| Core liquid | Purified water: | 100 parts | 0.22 ml/sec | — | 1.000 | 22.6° C. |
| Outer layer solution | Fatty acid ester of glycerin (melting point 42° C.): | 70 parts | 0.10 ml/sec | — | 0.943 | 70.0° C. |
| | Fatty acid ester of sucrose (melting point 36° C.): | 30 parts | | | | |
| Hardening soution | Purified water: HPC-H:* | 99.75 parts 0.25 parts | 9 cm/sec | 6 mPa · s | 1.002 | 32.0° C. |

*Nippon Soda Co. Ltd., see catalog for NISSO HYDROXY PROPYL CELLULOSE, also mentioned in the Pharmacopeia of Japan.

Hardnesses of the seamless capsules produced in Embodiments 1 to 3 and Comparative example were measured for each 50 capsules, and average values and CV (coefficient of variation) values were obtained. For measuring the hardness, a Schleuniger (trade name) tablet hardness tester, Model-4M was used.

The results of measuring the hardness are shown in Table 5. It is clearly seen that the hardnesses of the seamless capsules are much higher in the cases of Embodiments 1 to 3 than in Comparative example. From these results, it can be understood that the capsules of Embodiments 1 to 3 have good preservability and thus can be stored for a long period of time.

TABLE 5

| | Embodiment 1 | Embodiment 2 | Embodiment 3 | Comparative example |
|---|---|---|---|---|
| Hardness (kg/cm$^2$) | 2.1 | 1.9 | 3.2 | 0.9 |
| CV value (%) | 41 | 42 | 31 | 33 |

In this case, production was performed so that the capsule size was 5 mm in diameter, the outer layer thickness was 215 µm, the amount of the core solution was 47 mg and the capsule production rate was 30 capsules/sec. The production conditions are shown in Table 6. The average hardness of 50 capsules was 3.8 kg/cm$^2$ and the CV value was 39%.

Also, in the present Embodiment 4, it was found that the hardness of the capsule was high and preservability was good.

EMBODIMENT 4

By using the same apparatus as in Embodiments 1 to 3, seamless capsules of plum liqueur were produced.

TABLE 6

| | | Composition | | Flow rate or Flow speed | Viscosity | Specific gravity | Temperature |
|---|---|---|---|---|---|---|---|
| | | | Embodiment 4 | | | | |
| Core liquid | Plum liqueur: | | 100 parts | 1.38 ml/sec | — | 1.028 | 25.0° C. |
| Outer layer solution | Fatty acid ester of glycerin (melting point 42° C.): | | 50 parts | 0.59 ml/sec | — | 0.980 | 70.0° C. |
| | Fatty acid ester of sucrose (melting point 36° C.): | | 50 parts | | | | |
| Hardening soution | Purified water: HPC-H: | | 99 parts 1 parts | 9 cm/sec | 60 mPa · s | 1.005 | 23.0° C. |

EMBODIMENTS 5

By using the same apparatus as in Embodiments 1 to 4, seamless capsules of a Chinese medicine, Bupleurum Root extract were produced. In this production, the capsule size was 3.0 mm in diameter, the outer layer thickness was 129 μm, the amount of the core solution was 11.0 mg and the capsule production rate was 10 capsules/sec. The production conditions are shown in Table 7. The average hardness of 50 capsules was 3.2 kg/cm² and the CV value was 37%.

Also, in the present Embodiment 5, the hardness of the capsule was high and the preservability was good.

TABLE 7

| | | Composition | | Flow rate or Flow speed | Viscosity | Specific gravity | Temperature |
|---|---|---|---|---|---|---|---|
| | | | Embodiment 5 | | | | |
| Core liquid | *Bupleurem Root* extract: Purified water: | | 125 parts 75 parts | 0.11 ml/sec | — | 1.029 | 40.7° C. |
| Outer layer solution | Fatty acid ester of glycerin (melting point 42° C.): | | 50 parts | 0.10 ml/sec | — | 0.980 | 70.0° C. |
| | Fatty acid ester of sucrose (melting point 36° C.): | | 50 parts | | | | |
| Hardening soution | Purified water: HPC-H: | | 99 parts 1 parts | 9 cm/sec | 60 mPa · s | 1.005 | 32.0° C. |

Among the inventions disclosed in the present application, the effects obtained by the representative ones will be briefly explained as follows.

(1) According to the present invention, seamless capsules containing an aqueous solution and being able to endure a long period of preservation can be obtained.

(2) Also, according to the present invention, seamless capsules having a desired good shape can be obtained.

(3) Further, according to the present invention, seamless capsules having a uniform capsule size can be obtained.

Furthermore, the present invention should not be limited to the above embodiments, and various modifications are within the scope of the present invention.

What is claimed is:

1. A method of producing a seamless capsule, wherein, a two-layer droplet is ejected from a double orifice type nozzle into an aqueous hardening liquid, and an outer layer of the droplet is hardened under cooling, characterized in that a viscosity of said aqueous hardening liquid is within a range of 20 to 100 mPa·s.

2. The method according to claim 1, wherein the aqueous hardening liquid is an aqueous solution of a water-soluble polymer.

3. The method of producing a seamless capsule according to claim 1, wherein a droplet ejecting portion of the double orifice of the nozzle is dipped in the aqueous hardening liquid.

4. The method of producing a seamless capsule according to claim 1, wherein the nozzle is vibrated by a vibrating means.

5. A method of producing a seamless capsule, wherein a two-layer droplet is ejected from a double orifice type nozzle into an aqueous hardening liquid, and an outer layer of the droplet is hardened under cooling, characterized in that viscosity of the aqueous hardening liquid is within a range of 20 to 100 mPa·s and a difference in specific gravity between any two of liquids of layers ejected from the double orifice of the nozzle and the aqueous hardening liquid is within 0.05.

6. The method of producing a seamless capsule according to claim 5, wherein a droplet ejecting portion of the double orifice of the nozzle is dipped in the aqueous hardening liquid.

7. The method of producing a seamless capsule according to claim 5, wherein the nozzle is vibrated by a vibrating means.

* * * * *